(12) United States Patent
Prat et al.

(10) Patent No.: US 7,893,111 B2
(45) Date of Patent: *Feb. 22, 2011

(54) PROCESS FOR ENANTIOSELECTIVE SYNTHESIS OF SINGLE ENANTIOMERS OF THIO-SUBSTITUTED ARYLMETHANESULFINYL DERIVATIVES BY ASYMMETRIC OXIDATION

(75) Inventors: Laurence Prat, Pontault Combault (FR); Olivier Neckebrock, Pontault Combault (FR)

(73) Assignee: Cephalon France, Maisons-Alfort (FR)

( * ) Notice: Subject to any disclaimer, the term of this patent is extended or adjusted under 35 U.S.C. 154(b) by 625 days.

This patent is subject to a terminal disclaimer.

(21) Appl. No.: 11/374,227

(22) Filed: Mar. 13, 2006

(65) Prior Publication Data

US 2006/0205706 A1   Sep. 14, 2006

(30) Foreign Application Priority Data

Mar. 14, 2005 (EP) ................................. 05290560

(51) Int. Cl.
*A61K 31/165* (2006.01)
*C07C 323/29* (2006.01)

(52) U.S. Cl. ...................................... 514/618; 564/162

(58) Field of Classification Search ................. 514/618; 564/162
See application file for complete search history.

(56) References Cited

U.S. PATENT DOCUMENTS

| | | | |
|---|---|---|---|
| 4,098,824 A | 7/1978 | Lafon | 260/564 |
| 4,177,290 A | 12/1979 | Lafon | 424/324 |
| 4,927,855 A | 5/1990 | Lafon | 514/618 |
| 7,132,570 B2 | 11/2006 | Neckebrock et al. | |
| 7,211,684 B2 | 5/2007 | Rose et al | |
| 7,297,817 B2 * | 11/2007 | Lesur et al. | 564/162 |
| 7,317,126 B2 | 1/2008 | Rebiere et al. | |
| 7,368,591 B2 | 5/2008 | Rebiere et al. | |
| 7,449,481 B2 * | 11/2008 | Bacon et al. | 514/317 |
| 2006/0086667 A1 | 4/2006 | Hauck et al. | |
| 2007/0015836 A1 | 1/2007 | Rose | |
| 2009/0018143 A1 * | 1/2009 | Lesur et al. | 514/255.01 |

FOREIGN PATENT DOCUMENTS

| | | |
|---|---|---|
| EP | 1 477 476 A8 | 11/2004 |
| EP | 1 634 861 A1 | 3/2006 |
| FR | 2 381 862 | 2/1978 |
| WO | WO 03/101697 A2 | 12/2003 |
| WO | WO2004/060858 A1 | 7/2004 |
| WO | WO2004/063149 A1 | 7/2004 |
| WO | WO2005/028428 A1 | 3/2005 |

OTHER PUBLICATIONS

Abushanab, E., et al., "Sterospecific microbial oxidation of thioethers to sulfoxides. Application to the synthesis of R-Mevalonolactone," *Tetrahedron Lett.*, 1978, 37, 3415-3418.
Burgess, K., et al., "A facile route to homochiral sulfoxides," *Tetrahedron Letters*, 1989, 30(28), 3633-3636.
Cotton, H., et al., "Asymmetric synthesis of esomeprazole," *Tetrahedron: Asymmetry*, 2000, 11, 3819-3825.
Fernandez, I., et al., "Recent Developments in the Synthesis and Utilization of Chiral Sulfoxides", *Chem. Rev.*, 2003, 103(9), 3651-3706.
Holland, H.L., et al., "An investigation of the biotransformation of organic selenides by fungi," *Bioorg. Chem.*, 1983, 12, 1-7.
Holland, H.L., et al., "The oxidation of organic sulphides by *Mortierella isabellina*. 2. Effects of substituents on the stereochemistry of sulphoxide formation," *Can. J. Chem.*, 1985, 63, 1118-1120.
Kagan, H.B., "Asymmetric oxidation of sulfides," *Catalytic Asymmetric Synthesis*, Ojima, I. (Ed.), VCH, NY, 1993, 203-226.
Kagan, H.B., "Synthesis of chiral sulfoxides by asymmetric oxidation," *Phosphorus and Sulfur*, 1986, 27, 127-132.
Kagan, H.B., "Enantioselective oxidation of a sulfide: (S)-(-)-methyl p-tolyl sulfoxide," *Organic Syntheses*, John Wiley & Sons, Inc. (Ed.), 1993, vol. VIII, 464-467.
Madesclaire, M., "Synthesis of Sulfoxides by Oxidation of Thioethers", *Tetrahedron*, 1986, Report No. 210 42(20), 5459-5495.
Ohta, H., et al., "Microbial oxidation of alkyl aryl sulfides to the corresponding optically active sulfoxides," *Agrig. Biol. Chem.*, 1985, 49(3), 671-676.
Ohta, H., et al., "Microbial asymmetric oxidation of 2-alkoxyethylsulfides and a facile synthesis of chiral vinyl sulfoxide," *Chem. Lett.*, 1989, 625-628.
Pitchen, P. et al., "An Efficient Asymmetric Oxidation of Sulfides to Sulfoxides", *J. Am. Chem. Soc.*, 1984, 106, 8188-8193.
Procter, D., "The synthesis of thiols, selenols, sulfides, selenides, sulfoxides, selenoxides, sulfones and selenones," *J. Chem. Soc., Perkins Trans. 1*, 1999, 641-667.
Secundo, S., et al., "Asymmetric oxidation of sulfides by cyclohexanone monooxygenase," *Tetrahedron: Asymmetry*, 1993, 4(9), 1981-1982.
Zhao, S., et al., "Asymmetric oxidation of sulfides mediated by chiral titanium complexes: mechanistic and synthetic aspects," *Tetrahedron*, 1987, 43(21), 5135-5144.

* cited by examiner

Primary Examiner—Joseph R Kosack

(57) ABSTRACT

The invention relates to a method for preparing a sulphoxide compound of formula (I) either as a single enantiomer or in an enantiomerically enriched form, comprising the steps of:
  a) contacting a pro-chiral sulphide of formula (II) with a metal chiral complex, a base and an oxidizing agent in an organic solvent; and optionally
  b) isolating the obtained sulphoxide of formula (I).

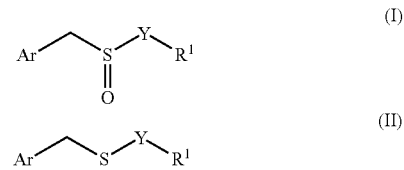

wherein Ar, Y, $R^1$ are as defined in claim 1.

17 Claims, No Drawings

PROCESS FOR ENANTIOSELECTIVE SYNTHESIS OF SINGLE ENANTIOMERS OF THIO-SUBSTITUTED ARYLMETHANESULFINYL DERIVATIVES BY ASYMMETRIC OXIDATION

The present invention relates to a process for enantioselective synthesis of the single enantiomers or an enantiomerically enriched form of arylmethane-sulphinyl derivatives.

BACKGROUND OF THE INVENTION

The compounds disclosed herein are synthetic arylmethanesulphinyl derivatives related to the biological and chemical analogs of modafinil. Modafinil, $C_{15}H_{15}NO_2S$, also known as 2-(benzhydrylsulphinyl) acetamide, or 2-[(diphenylmethyl) sulphinyl]acetamide, a synthetic acetamide derivative with wake-promoting activity, has been described in French Patent No. 78 05 510 and in U.S. Pat. No. 4,177,290 ("the '290 patent"). All these molecules share in common, in their structure, a stereogenic center at the sulfur atom and therefore exist as pair of enantiomers. Both enantiomers may exhibit differential stereochemically dependent metabolism and enzyme inhibition. Due to FDA and Registration Agencies policy statement regarding the development of new stereoisomeric drugs, both enantiomers of pharmaceutically interesting chiral sulphoxides need to be synthesized and their biological activity determined. The synthesis of chiral sulphoxides with high enantiomeric purity is presently of interest.

The enantiomers may be processed by chiral resolution methods, which imply salt formation of an acid racemate compounds. The resulting diastereoisomers have to be separated and converted into the optically pure enantiomers by hydrolysis or bond cleavage. These methods are generally time consuming. As an example, such a method was applied to modafinil enantiomers (U.S. Pat. No. 4,927,855). The levorotary isomer of modafinic acid was obtained with very poor yields of about 21% from racemic modafinic acid and had to be further processed by esterification and amidation steps, before the single enantiomer of the required amide modafinil was obtained.

Considering alternative ways of obtaining enantiomerically pure arylmethanesulphinyl derivatives various metal-catalyzed enantioselective oxidations or stoichiometric transition-metal-promoted asymmetric reactions were described in the literature to prepare chiral sulphoxides by chemical oxidation of the corresponding sulphides (Kagan H. B. In "Catalytic Asymmetric Synthesis"; Ojima I., Ed. VCH: New York 1993, 203-226; Madesclaire M., Tetrahedron 1986; 42, 5459-5495; Procter D., J. Chem. Soc. PerkinTrans 1999; 641-667; Fernandez I. et al., Chem. Review 2003; 103(9): 3651-3706. Metal-catalyzed enantioselective oxidations involve a metal catalyst complexed with a chiral ligand such as diethyl tartrate, $C_2$-symmetric diols or $C_3$-symmetric chiral trialkanolamine titanium(IV) complexes, $C_3$-symmetric trialkanolamine zirconium(IV) complex, chiral (salen) manganese(III) complex, chiral (salen) vanadium(IV) complex in the presence of various oxidants such as $H_2O_2$, tert-butyl hydroperoxide, cumene hydroperoxide. Methods based on chiral oxaziridines have also been used in the chemical oxidation of sulphides.

Some enzymatic methods for the asymmetric synthesis of fine chemicals were described in Faber K. in "Biotransformations in Organic Chemistry", Springer Ed. $3^{rd}$ ed. 1997 and reviewed by Fernandez I. et al. (Chem. Rev. 2003; 103(9): 3651-3706). As an example, thioethers can be asymmetrically oxidized both by bacteria [e.g. *Corynebacterium equi* (Ohta H. et al. Agrig. Biol. Chem. 1985; 49: 671), *Rhodococcus equi* (Ohta H. et al. Chem. Left. 1989; 625)] and fungi [*Helminthosporium* sp., *Mortieralla isabellina* sp. (Holland H L. et al. Bioorg. Chem. 1983; 12:1)]. A large variety of aryl alkyl thioethers were oxidized to yield sulphoxides with good to excellent optical purity [(Ohta H. et al. Agrig. Biol. Chem. 1985; 49:671; Abushanab E. et al., Tetrahedron Lett. 1978; 19:3415; Holland H L. et al. Can. J. Chem. 1985; 63:1118)]. Mono-oxygenases and peroxidases are important class of enzymes able to catalyse the oxidation of a variety of sulphides into sulphoxides (Secundo S. et al. Tetrahedron: Asymmetry 1993; 4:1981). The stereochemical outcome of the enzymatic reactions has been shown to be highly dependant on the sulphide structure.

As an other alternative of the enzymatic approach, optically pure methyl arylsulphinylacetates with high enantiomeric excess (>98%) obtained by lipase-catalyzed resolution of the corresponding racemate were also described (Burgess K. et al. Tetrahedron Letter 1989; 30: 3633).

As an enantioselective oxidation method, an asymmetric sulphide oxidation process has been developed by Kagan and co-workers (Pitchen, P; Deshmukh, M., Dunach, E.; Kagan, H. B.; J. Am. Chem. Soc., 1984; 106, 8188-8193). In this process for asymmetric oxidation of sulphides to sulphoxides, the oxidation is performed by using tert-butyl hydroperoxide (TBHP) as oxidizing agent in the presence of one equivalent of a chiral complex obtained from $Ti(OiPr)_4$, (+) or (−) diethyl tartrate/water in the molar ratio 1:2:1.

The general procedure for sulphide oxidation according to Kagan comprises first preforming the chiral complex at room temperature in methylene chloride before adding the sulphide. Then, the oxidation reaction is effected at −20° C. in the presence of tert-butyl hydroperoxide.

The direct oxidation of a variety of sulphides, notably for arylalkyl sulphides into optically active sulphoxides, with an enantiomeric excess (ee), in the range of 80-90%, can be achieved by this method.

More specifically, Kagan and co-workers reported that sulphoxide products could be obtained with high enantioselectivity when sulphides bearing two substituents of very different size were subjected to an asymmetric oxidation. For instance, when aryl methyl sulphides were subjected to oxidation, it was possible to obtain the aryl methyl sulphoxides in an enantiomeric excess (ee) of more than 90%.

Notably, cyclopropylphenyl sulphoxide is formed with 95% ee by this method.

However, asymmetric oxidation of functionalized sulphides, notably those bearing an ester function, was found to proceed with moderate enantioselectivity under these conditions.

Thus, compounds bearing on the stereogenic center, i.e. the sulphur atom, an alkyl moiety with an ester function close to the sulphur atom, such as methylphenylthioacetate, ethylmethylthioacetate and methylmethylthiopropanoate, are reported with ee of only 63-64% (H. B. Kagan, Phosphorus and Sulphur, 1986; 27, 127-132).

Similarly, oxidation of the aryl methyl sulphides with a methyl ester function in the ortho position of the aryl group yields low enantiomeric excess (60%) and yield (50%) as compared to the para substituted compound (ee 91%, yield 50%) or to the p-tolyl methyl sulphide (ee 91%, yield 90%) (Pitchen, P et al., J. Am. Chem. Soc., 1984; 106, 8188-8193).

Hence, even when the substituents on the sulphur atom differ in size, the presence of an ester function close to the sulphur atom strongly affects the enantioselectivity of the asymmetric oxidation.

These results also show that the enantioselectivity of this process is highly depends on the structure and notably on the functionality of the substrate. More specifically, oxidation of sulphides bearing an ester function close to the sulphur gives little asymmetric induction.

Similarly, none of the enantioselective reactions so far reported in the literature deals with substrates bearing an acetamide or acetic acid moiety directly linked to the sulphur atom.

There have been attempts to improve the enantioselectivity by modifying some conditions for asymmetric oxidation of sulphides. For example, Kagan and co-workers (Zhao, S.; Samuel O.; Kagan, H. B., Tetrahedron 1987; 43, (21), 5135-5144) found that the enantioselectivity of oxidation could be enhanced by using cumene hydroperoxide instead of tert-butyl hydroperoxide (ee up to 96%). However, these conditions do not solve the problem of oxidation of sulphides bearing ester, amide or carboxylic acid functions close to the sulphur atom.

Thus, the applicant obtained crude (−)-modafinil with a typical enantiomeric excess of at most about 42% with the above method using the conditions described by Kagan H. B. (Organic Syntheses, John Wiley and Sons INC. ed. 1993, vol. VIII, 464-467).

H. Cotton and co-workers (Tetrahedron: Asymmetry 2000; 11, 3819-3825) recently reported a synthesis of the (S)-enantiomer of omeprazole via asymmetric oxidation of the corresponding prochiral sulphide. Omeprazole, also called 5-methoxy-2-[[(4-methoxy-3,5-dimethyl-2pyridinyl)methyl]-sulphinyl]-1H-benzimidazole is represented by the following formula:

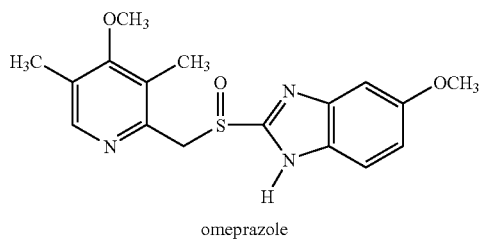

omeprazole

The asymmetric oxidation was achieved by titanium-mediated oxidation with cumene hydroperoxide (CHP) in the presence of (S,S)-(−) diethyl tartrate [(S,S)-(−)-DET]. The titanium complex was prepared in the presence of the prochiral sulphide and/or during a prolonged time and by performing the oxidation in the presence of N,N-diisopropylethylamine. An enantioselectivity of >94% was obtained by this method, whereas the Kagan's original method gives a modest enantiomeric excess of the crude product (30%).

According to the authors, the improved enantioselectivity of this process applied to omeprazole only is probably linked to the presence of benzimidazole or imidazole group adjacent to sulphur, which steers the stereochemistry of formed sulphoxide. The authors also suggested using this kind of functionality as directing groups when synthesizing chiral sulphoxides in asymmetric synthesis.

Hence, this publication is essentially focused on omeprazole, a pro-chiral sulphide bearing substituents of approximately the same size, and including an imidazole group which is described to play an important role in the asymmetric induction.

Therefore, there is a need for an improved enantioselective process for the manufacture of optically pure arylmethanesulphinyl derivatives which overcomes the drawbacks of the prior art and, in particular, allows high yields.

BRIEF DESCRIPTION OF THE INVENTION

The present invention provides a novel process for enantioselective synthesis of the single enantiomers of arylmethanesulphinyl derivatives, in which process a surprisingly high enantioselectivity along with a high yield is obtained.

The novel process is characterized in that a pro-chiral sulphide is oxidized asymmetrically into a single enantiomer or an enantiomerically enriched form of the corresponding sulphoxide.

The invention also provides a process for preparing a sulphoxide as a single enantiomer or an enantiomerically enriched form from the corresponding pro-chiral sulphide with high purity, advantageously with a purity greater than 97-98%.

The expression "pro-chiral sulphide(s)", as used herein, is understood to designate sulphides which after oxidation present a stereogenic center on the sulphur atom. Sulphides having further stereogenic centers elsewhere are thus also herein referred to as "pro-chiral sulphides".

This novel asymmetric oxidation process allows access to the compounds of interest with an extremely high enantiomeric excess, even if the corresponding pro-chiral sulphides are functionalized, i.e. have ester, amide, carboxylic acid or nitrile substituents.

The process is simple with a one step reaction making the process suitable for large scale production of enantiomeric compounds in a high yield and high enantiomeric excess.

As a further advantage, this process implements low amounts of a titanium compound as a catalyst which is environmentally non-toxic and relatively low-cost.

Advantageously, the arylmethanesulphinyl derivative can be obtained as a single enantiomer or in an enantiomerically enriched form, more directly, without having to go through classical chiral resolution methods.

The invention also provides several processes for preparing arylmethane-sulphinyl acetamide as a single enantiomer or in an enantiomerically enriched form. Advantageously, these processes are limited to three steps or even less when using the appropriate aryl alcohol or thiol as starting material.

DETAILED DESCRIPTION OF THE INVENTION

It has been found that the asymmetric oxidation of arylmethanesulphinyl derivatives precursors, in particular arylmethanesulphinyl acetic acids, the amides and the esters thereof could be achieved with surprisingly high enantioselectivity up to 96% and the more, by effecting the titanium chiral complex mediated reaction in the presence of a base.

In a first embodiment, the invention relates to a method for preparing a sulphoxide compound of formula (I) either as a single enantiomer or in an enantiomerically enriched form:

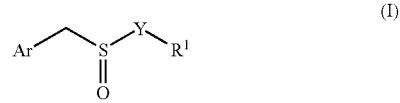

wherein:
Ar is:

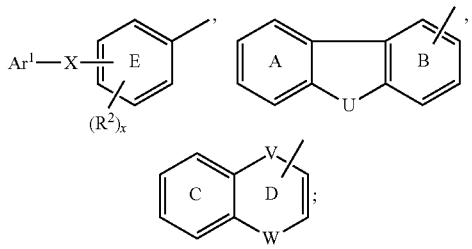

wherein:
- U, V and W are independently selected from a bond, $CH_2$, $CR^{23}R^{24}$, O, $S(O)_y$, $NR^{11}$, $C(=O)$, CHOH, $CHOR^{14}$, $C=NOR^{14}$, or $C=NNR^{12}R^{13}$;
- Rings A, B, and C are optionally substituted with one to three groups selected from H, F, Cl, Br, I, $OR^{22}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, and $NR^{21}C(=S)R^{22}$;
- Ring D is optionally substituted with one group selected from $C_1$-$C_6$ alkyl, phenyl, and 5-10 membered heteroaryl;
- X is a bond, O, $NR^{11}$, $OC(R^{22})_2$, $C(R^{22})_2O$, $C(R^{22})_2NR^{21}$, $NR^{21}C(R^{22})_2$, $C(=O)NR^{21}$, $NR^{21}C(=O)$, $S(O)_2NR^{22}$, $NR^{22}S(O)_2$, $C(R^{22})_2C(R^{22})_2$, $CR^{21}=CR^{21}$, $C≡C$;
- $R^2$ is selected from H, F, Cl, Br, I, $OR^{16}$, $NR^{17}R^{18}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, alkynyl, $C(=O)R^{16}$, $CO_2R^{16}$, $OC(=O)R^{16}$, $C(=O)NR^{17}R^{18}$, $NR^{15}C(=O)R^{16}$, $NR^{15}CO_2R^{16}$, $OC(=O)NR^{17}R^{18}$ and $NR^{15}C(=S)R^{16}$;
- alternatively, two $R^2$ groups may be combined to form a methylenedioxy group, an ethylenedioxy group, or a propylenedioxy group.
- $Ar^1$ is $C_6$-$C_{10}$ aryl optionally substituted by 0-5 $R^3$;
  - $C_5$-$C_{10}$ cycloalkenyl optionally substituted by 0-5 $R^3$;
  - $C_5$-$C_{10}$ membered heteroaryl group optionally substituted by 0-5 $R^3$; wherein said heteroaryl comprises one, two, or three heteroatoms selected from N, O, S, or Se;
  wherein:
  - $R^3$ is selected from H, F, Cl, Br, I, $OR^{16}$, $OCF_3$, $NR^{17}R^{18}$, NHOH, $NO_2$, CN, $CF_3$, $CH_2OR^{16}$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, $C_7$-$C_{10}$ arylalkyl, $C(=O)R^{16}$, $CO_2R^{16}$, $OC(=O)R^{16}$, $C(=O)NR^{17}R^{18}$, $NR^{15}C(=O)R^{16}$, $NR^{15}CO_2R^{16}$, $OC(=O)NR^{17}R^{18}$, $NR^{15}C(=S)R^{16}$, and $NR^{15}S(=O)_2R^{16}$;
  alternatively, two $R^3$ groups may be combined to form a methylenedioxy group, an ethylenedioxy group, or a propylenedioxy group;
- Y is $C_1$-$C_6$ alkylene;
- $R^1$ is selected from CN, $C(=O)R^{14}$, $CO_2R^{11}$, $C(=O)NR^{12}R^{13}$, $C(=O)NR^{21}OR^{22}$, $C(=NR^{11})NR^{12}R^{13}$, $OC(=O)R^{11}$, $OC(=O)NR^{12}R^{13}$, $NR^{12}R^{13}$, $NR^{21}NR^{12}R^{13}$, $NR^{21}C(=O)R^{14}$, $NR^{21}C(=O)NR^{12}R^{13}$, $NR^{21}S(O)_2R^{11}$, $NR^{21}S(O)_2NR^{12}R^{13}$.
- $R^{11}$ at each occurrence is independently selected from H, $C_1$-$C_6$ alkyl, $C_3$-$C_7$ cycloalkyl, $C_6$-$C_{10}$ aryl, arylalkyl; wherein said alkyl, aryl, arylalkyl groups are optionally substituted with one to three $R^{20}$ groups;
- $R^{12}$ and $R^{13}$ at each occurrence are each independently selected from H, $C_1$-$C_6$ alkyl, $C_6$-$C_{10}$ aryl, and $NR^{23}R^{24}$, or $R^{12}$ and $R^{13}$, together with the nitrogen to which they are attached, form a 3-7 membered heterocyclic ring; wherein said alkyl and aryl groups and heterocyclic ring are optionally substituted with one to three $R^{20}$ groups;
- $R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted.
- $R^{15}$ at each occurrence is independently selected from H, $C_1$-$C_6$ alkyl;
- $R^{16}$ at each occurrence is independently selected from H, $C_1$-$C_6$ alkyl, and $C_6$-$C_{10}$ aryl; wherein said alkyl and aryl groups are optionally substituted with one to three $R^{20}$ groups;
- $R^{17}$ and $R^{18}$ at each occurrence are each independently selected from H, $C_1$-$C_6$ alkyl, and $C_6$-$C_{10}$ aryl, or $R^{17}$ and $R^{18}$, together with the nitrogen to which they are attached, form a 3-7 membered heterocyclic ring; wherein said alkyl and aryl groups and heterocyclic ring are optionally substituted with one to two oxo groups;
- $R^{20}$ at each occurrence is independently selected from F, Cl, Br, I, $OR^{22}$, $NR^{23}R^{24}$, NHOH, $NO_2$, CN, $CF_3$, $C_1$-$C_6$ alkyl optionally substituted by one to three OH, $C_2$-$C_6$ alkenyl, $C_2$-$C_6$ alkynyl, $C_3$-$C_7$ cycloalkyl, 3-7 membered heterocycloalkyl, phenyl substituted by zero to one $OR^{25}$, 5 or 6 membered heteroaryl, arylalkyl, =O, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, and $OC(=O)NR^{23}R^{24}$;
- $R^{21}$ at each occurrence is independently selected from H and $C_1$-$C_6$ alkyl;
- $R^{22}$ at each occurrence is independently selected from H, $C_1$-$C_6$ alkyl, $C_1$-$C_6$ alkyl-OH and $C_6$-$C_{10}$ aryl;
- $R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocyclic ring optionally substituted with one to three oxo groups;
- $R^{25}$ at each occurrence is independently selected from H, F, Cl, Br, $C_1$-$C_6$ alkyl, $C_1$-$C_6$ and alkyloxy;
- x is 1, 2, 3 or 4;
- y is 0, 1 or 2;
- comprising the steps of:
  a) contacting a pro-chiral sulphide of formula (II)

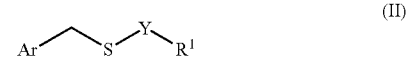

(II)

wherein Ar, Y and $R^1$ are as defined above,
with a metal chiral ligand complex, a base and an oxidizing agent in an organic solvent; and optionally
b) isolating the obtained sulphoxide of formula (I).

The method allows to prepare sulphoxides of formula (I) with an enantiomeric excess of generally more than about 80%. Advantageously, preferred enantiomeric excess is of more than 80%, preferably of more than 90%, more preferably of more than 95%, and most preferably of 99% and more.

The method allows also to prepare sulphoxides of formula (I) with a degree of purity higher than 90%, preferably of more than 98%, more preferably superior to 99%.

For a pair of enantiomers, enantiomeric excess (ee) of enantiomer E1 in relation to enantiomer E2 can be calculated using the following equation:

$$\% \text{ enantiomeric excess} = \frac{(E1 - E2)}{(E1 + E2)} \times 100$$

The relative amount of E1 and E2 can be determined by chiral HPLC (High Performance Liquid Chromatography).

The purity refers to the amount of the enantiomers E1 and E2, relative to the amount of other materials, which may notably include by-products such as sulphone, and the unreacted sulphide. The purity may be determined by HPLC as well.

As used herein, the term "about" refers to a range of values ±10% of the specified value. For example, "about 20" includes ±10% of 20, or from 18 to 22.

As used herein, the term "a metal chiral ligand complex" refers to a complex composed of a metal compound, a chiral ligand and, optionally, water.

The term "chiral ligand" is a group which includes at least one chiral center and has an absolute configuration. A chiral ligand has a (+) or (−) rotation of plane polarized light.

As used herein, the term "alkyl" refers to a straight-chain, or branched, alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons, such as methyl, ethyl, propyl, isopropyl, butyl, isobutyl, sec-butyl, and tert-butyl. A designation such as "$C_1$-$C_4$ alkyl" refers to an alkyl radical containing from 1 to 4 carbon atoms.

As used herein, the term "alkenyl" refers to a straight-chain, or branched, hydrocarbon group of 2 to 6 carbon atoms having at least one carbon-carbon double bond. A designation "$C_2$-$C_6$ alkenyl" refers to an alkenyl radical containing from 2 to 6 carbon atoms. Examples of alkenyl groups include, but are not limited to, ethenyl, propenyl, isopropenyl, butenyl, pentenyl, 2,4-pentadienyl, etc. Preferred alkenyl groups include ethenyl and propenyl.

As used herein, the term "alkynyl" refers to a straight chain, or branched hydrocarbon chains of 2 to 6 carbon atoms having at least one carbon-carbon triple bond. A designation "$C_2$-$C_6$ alkynyl" refers to an alkynyl radical containing from 2 to 6 carbon atoms. Examples include, but are not limited to, ethynyl, propynyl, isopropynyl, 3,5-hexadiynyl, etc.

As used herein, the term "alkylene" refers to a substituted or unsubstituted, branched or straight chained hydrocarbon of 1 to 6 carbon atoms, which is formed by the removal of two hydrogen atoms. A designation such as "$C_1$-$C_4$ alkylene" refers to an alkylene radical containing from 1 to 4 carbon atoms. Examples include, but are not limited to, methylene (—$CH_2$—), ethylene (—$CH_2CH_2$—), ethylidene (—CH($CH_3$)—), propylene (—$CH_2CH_2CH_2$—), iso-propylene (—CH($CH_3$)$CH_2$—), propylidene (—CH($CH_2CH_3$)—), butylene (—$CH_2CH_2CH_2CH_2$—), etc.

As used herein, the term "cycloalkylene" refers to a saturated or partially saturated mono- or bicyclic alkyl ring system containing 3 to 10 carbon atoms, which is formed by the removal of two hydrogen atoms. A designation such as "$C_3$-$C_6$ cycloalkylene" refers to a cycloalkyl radical containing from 3 to 6 ring carbon atoms. Preferred cycloalkylene groups include those containing 3, 4, 5, or 6 ring carbon atoms. Examples of cycloalkylene groups include such groups as cyclopropylene (—$C_3H_4$—), cyclobutylene (—$C_4H_6$—), cyclopentylene (—$C_5H_8$—), cyclopentenylene (—$C_5H_6$—), cyclohexylene (—$C_6H_{10}$—), and cyclohexenylene (—$C_6H_8$—).

As used herein, the term "phenylene" refers to a phenyl group with an additional hydrogen atom removed, i.e. a moiety with the structure of (—$C_6H_4$—).

As used herein, the terms "carbocycle", "carbocyclic" or "carbocyclyl" refer to a substituted or unsubstituted, stable monocyclic or bicyclic hydrocarbon ring system which is saturated, partially saturated or unsaturated, and contains from 3 to 10 ring carbon atoms. Accordingly, the carbocyclic group may be aromatic or non-aromatic, and includes the cycloalkyl and aryl compounds defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms. A designation such as "$C_3$-$C_7$ cycloalkyl" refers to a cycloalkyl radical containing from 3 to 7 ring carbon atoms. Preferred cycloalkyl groups include those containing 3, 4, 5, or 6 ring carbon atoms. Examples of cycloalkyl groups include such groups as cyclopropyl, cyclobutyl, cyclopentyl, cyclohexl, cycloheptyl, cyclooctyl, pinenyl, and adamantanyl.

As used herein, the term "cycloalkenyl" refers to partially unsaturated mono- or bicyclic alkenyl ring system containing 5 to 10 carbon atoms. A designation such as "$C_5$-$C_{10}$ cycloalkenyl" refers to a cycloalkenyl radical containing from 5 to 10 ring carbon atoms and one or more double bonds. Preferred cycloalkenyl groups include those containing 5 or 7 ring carbon atoms. Examples of cycloalkenyl groups include such groups as cyclopentenyl, cyclohexenyl, and cycloheptenyl.

As used herein, the term "aryl" refers to a substituted or unsubstituted, mono- or bicyclic hydrocarbon aromatic ring system having 6 to 10 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the term "arylene" refers to an aryl group with an additional hydrogen atom removed, i.e. an aryl group bonded through two carbon atoms, for example phenylene.

As used herein, the term "heteroarylene" refers to a heteroaryl group with an additional hydrogen atom removed, i.e. a heteroaryl group bonded through two carbon atoms, for example furan-2,5-diyl; or a heteroaryl group bonded through a carbon atom and a nitrogen atom, for example pyrrol-1,2-diyl.

As used herein, the term "heterocycloalkylene" refers to a heterocycloalkyl group with an additional hydrogen atom removed, i.e. a heterocycloalkyl group bonded through two carbon atoms or a heterocycloalkyl group bonded through a carbon atom and a nitrogen atom.

As used herein, the terms "heterocycle", "heterocyclic" or "heterocyclyl" refer to a substituted or unsubstituted carbocyclic group in which the ring portion includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups. Examples of heterocyclic groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl, as well as, pyrrolidinyl, pyrrolinyl, imidazolidinyl, imidazolinyl, pyrazolidinyl, pyrazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl.

As used herein, the term "heterocycloalkyl" refers to a 3 to 7 membered cycloalkyl group in which one or more ring carbon atoms are replaced by at least one hetero atom such as —O—, —N—, or —S—. Examples of heterocycloalkyl groups include pyrrolidinyl, pyrrolinyl, imidazolidinyl, imidazolinyl, pirazolidinyl, pirazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl.

As used herein, the term "heteroaryl" refers to an aromatic group containing 5 to 14 ring carbon atoms in which one or more ring carbon atoms are replaced by at least one hetero atom such as —O—, —N—, —S—, or —Se—. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, picolinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "arylalkyl" refers to an alkyl group that is substituted with an aryl group. A designation "$C_7$-$C_{10}$ arylalkyl" refers to an alkyl group that is substituted with an aryl group with the combination thereof containing from 7 to 10 carbon atoms. Examples of arylalkyl groups include, but are not limited to, benzyl, phenethyl, phenylpropyl, diphenylmethyl, triphenylmethyl, diphenylethyl, naphthylmethyl, etc. Preferred examples of arylalkyl groups include, but are not limited to, benzyl, and phenethyl.

In the case of $R^1$ is C(=O)OH, the sulphoxide of formula (I) may be obtained as a salt, notably as an alkaline salt, such as a sodium, potassium, lithium salt or ammonium salt or pharmaceutically acceptable salts.

As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, paratoluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker: New York, 1992, incorporated by reference herein in its entirety As used herein, "between [ . . . ]-[ . . . ]" refers to an inclusive range.

In another preferred embodiment, the invention relates to a method for preparing a sulphoxide compound of formula (Ia) either as a single enantiomer or in an enantiomerically enriched form:

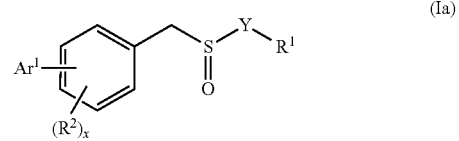

(Ia)

wherein:
  $Ar^1$ is $C_6$-$C_{10}$ aryl optionally substituted by 0-5 $R^3$;
    $C_5$-$C_{10}$ cycloalkenyl optionally substituted by 0-5 $R^3$;
    $C_5$-$C_{10}$ membered heteroaryl group optionally substituted by 0-5 $R^3$; wherein said heteroaryl comprises one, two, or three heteroatoms selected from N, O, S, or Se;
wherein:
  $R^3$ is selected from H, F, Cl, Br, I, $OR^{16}$, $OCF_3$, $NR^{17}R^{18}$, NHOH, $NO_2$, CN, $CF_3$, $CH_2OR^{16}$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, $C_7$-$C_{10}$ arylalkyl, C(=O)$R^{16}$, $CO_2R^{16}$, OC(=O)R$^{16}$, C(=O)NR$^{17}$R$^{18}$, NR$^{15}$C(=O)R$^{16}$, NR$^{15}$CO$_2$R$^{16}$, and O(C=O)NR$^{17}$R$^{18}$;

alternatively, two R$^3$ groups may be combined to form a methylenedioxy group, an ethylenedioxy group, or a propylenedioxy group;

Y is C$_1$-C$_6$alkylene;

R$^1$ is selected from CN, C(=O)R$^{14}$, CO$_2$R$^{11}$, C(=O)NR$^{12}$R$^{13}$, C(=O)NR$^{21}$OR$^{22}$, OC(=O)R$^{11}$, OC(=O)NR$^{12}$R$^{13}$, NR$^{12}$R$^{13}$, NR$^{21}$NR$^{12}$R$^{13}$, NR$^{21}$C(=O)R$^{14}$, NR$^{21}$C(=O)NR$^{12}$R$^{13}$;

R$^2$ is selected from H, F, Cl, Br, I, OR$^{16}$, NR$^{17}$R$^{18}$, NHOH, NO$_2$, CN, CF$_3$, C$_1$-C$_6$ alkyl, C$_2$-C$_6$ alkenyl, C$_2$-C$_6$ alkynyl, C$_3$-C$_7$ cycloalkyl, C(=O)R$^{16}$, CO$_2$R$^{16}$, OC(=O)R$^{16}$, C(=O)NR$^{17}$R$^{18}$, NR$^{15}$C(=O)R$^{16}$, NR$^{15}$CO$_2$R$^{16}$, and OC(=O)NR$^{17}$R$^{18}$, and NR$^{15}$C(=S)R$^{16}$;

alternatively, two R$^2$ groups may be combined to form a methylenedioxy group, an ethylenedioxy group, or a propylenedioxy group;

R$^{11}$ at each occurrence is independently selected from H, C$_1$-C$_6$ alkyl, C$_3$-C$_7$ cycloalkyl, C$_6$-C$_{10}$ aryl, arylalkyl; wherein said alkyl, aryl, arylalkyl groups are optionally substituted with one to three R$^{20}$ groups;

R$^{12}$ and R$^{13}$ at each occurrence are each independently selected from H, C$_1$-C$_6$ alkyl, C$_6$-C$_{10}$ aryl, and NR$^{23}$R$^{24}$, or R$^{12}$ and R$^{13}$, together with the nitrogen to which they are attached, form a 3-7 membered heterocyclic ring;
wherein said alkyl and aryl groups and heterocyclic ring are optionally substituted with one to three R$^{20}$ groups;

R$^{14}$ at each occurrence is independently selected from C$_1$-C$_6$ alkyl, C$_6$-C$_{10}$ aryl, and arylalkyl; wherein said alkyl, aryl and arylalkyl groups are optionally substituted with one to three R$^{20}$ groups;

R$^{15}$ at each occurrence is independently selected from H, C$_1$-C$_6$ alkyl;

R$^{16}$ at each occurrence is independently selected from H, C$_1$-C$_6$ alkyl, and C$_6$-C$_{10}$ aryl; wherein said alkyl and aryl groups are optionally substituted with one to three R$^{20}$ groups;

R$^{17}$ and R$^{18}$ at each occurrence are each independently selected from H, C$_1$-C$_6$ alkyl, and C$_6$-C$_{10}$ aryl, or R$^{17}$ and R$^{18}$, together with the nitrogen to which they are attached, form a 3-7 membered heterocyclic ring;
wherein said alkyl and aryl groups and heterocyclic ring are optionally substituted with one to two oxo groups;

R$^{20}$ at each occurrence is independently selected from F, Cl, Br, I, OR$^{22}$, NR$^{23}$R$^{24}$, NHOH, NO$_2$, CN, CF$_3$, C$_1$-C$_6$ alkyl optionally substituted by one to three OH, C$_2$-C$_6$ alkenyl, C$_2$-C$_6$ alkynyl, C$_3$-C$_7$ cycloalkyl, 3-7 membered heterocycloalkyl, phenyl substituted by zero to one OR$^{25}$, 5 or 6 membered heteroaryl, arylalkyl, =O, C(=O)R$^{22}$, CO$_2$R$^{22}$, OC(=O)R$^{22}$, C(=O)NR$^{23}$R$^{24}$, NR$^{21}$C(=O)R$^{22}$, NR$^{21}$CO$_2$R$^{22}$, and OC(=O)NR$^{23}$R$^{24}$;

R$^{21}$ at each occurrence is independently selected from H and C$_1$-C$_6$ alkyl;

R$^{22}$ at each occurrence is independently selected from H, C$_1$-C$_6$ alkyl, C$_1$-C$_6$ alkyl-OH and C$_6$-C$_{10}$ aryl;

R$^{23}$ and R$^{24}$ at each occurrence are each independently selected from H, C$_1$-C$_6$ alkyl, and C$_6$-C$_{10}$ aryl, or R$^{23}$ and R$^{24}$, together with the nitrogen to which they are attached, form a 3-7 membered heterocyclic ring optionally substituted with one to three oxo groups;

R$^{25}$ at each occurrence is independently selected from H, F, Cl, Br, C$_1$-C$_6$ alkyl, C$_1$-C$_6$ alkyloxy;

x is 1, 2, 3 or 4;

comprising the steps of:
a) contacting a pro-chiral sulphide of formula (IIa)

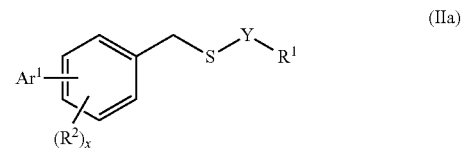

(IIa)

wherein Ar$^1$, Y, R$^1$, R$^2$ and x are as defined above,
with a metal chiral ligand complex, a base and an oxidizing agent in an organic solvent; and optionally
b) isolating the obtained sulphoxide of formula (Ia).

Preferably, the sulphoxide prepared according to the invention is a sulphoxide of formula (Ia) wherein:

Ar$^1$ is a C$_6$-C$_{10}$ aryl substituted by 0-5 R$^3$ or a 5 to 14 membered heteroaryl group substituted by 0-5 R$^3$, wherein said heteroaryl group comprises one, two, or three heteroatoms selected from N, O, S or Se. Preferably, said C$_6$-C$_{10}$ aryl is a phenyl and said 5 to 14 membered heteroaryl group is selected from phenoxathiinyl, pyrimidinyl, quinolinyl, isoxazolyl, thienyl, benzothienyl, (1,1-dioxo)-benzothienyl, indolyl, furyl, benzofuryl, pyridyl, seleninyl, 1,3-dihydro-isoindolyl, pyrrolyl, and 2-benzo[1,4]dioxine.

In another preferred embodiment, the invention relates to a method for preparing a sulphoxide compound of formula (Ib) either as a single enantiomer or in an enantiomerically enriched form:

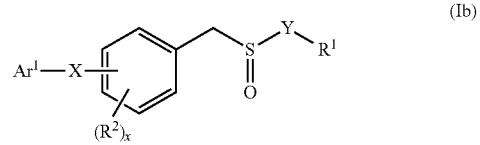

(Ib)

wherein:
Ar$^1$ is C$_6$-C$_{10}$ aryl optionally substituted by 0-5 R$^3$;
C$_5$-C$_{10}$ cycloalkenyl optionally substituted by 0-5 R$^3$;
C$_5$-C$_{10}$ membered heteroaryl group optionally substituted by 0-5 R$^3$; wherein said heteroaryl comprises one, two, or three heteroatoms selected from N, O, S, or Se;

wherein:
R$^3$ is selected from H, F, Cl, Br, I, OR$^{16}$, OCF$_3$, NR$^{17}$R$^{18}$, NHOH, NO$_2$, CN, CF$_3$, CH$_2$OR$^{16}$, C$_1$-C$_6$ alkyl, C$_2$-C$_6$ alkenyl, C$_2$-C$_6$ alkynyl, C$_3$-C$_7$ cycloalkyl, 3-7 membered heterocycloalkyl, phenyl, 5 or 6 membered heteroaryl, C$_7$-C$_{10}$ arylalkyl, C(=O)R$^{16}$, CO$_2$R$^{16}$, OC(=O)R$^{16}$, C(=O)NR$^{17}$R$^{18}$, NR$^{15}$C(=O)R$^{16}$, NR$^{15}$CO$_2$R$^{16}$, and OC(=O)NR$^{17}$R$^{18}$;

alternatively, two R$^3$ groups may be combined to form a methylenedioxy group, an ethylenedioxy group, or a propylenedioxy group;

X is O, S(O)$_2$, NR$^{11}$, OC(R$^{22}$)$_2$, C(R$^{22}$)$_2$O, C(R$^{22}$)$_2$NR$^{21}$, NR$^{21}$C(R$^{22}$)$_2$, C(=O)NR$^{21}$, NR$^{21}$C(=O), S(O)$_2$NR$^{22}$, NR$^{22}$S(O)$_2$, C(R$^{22}$)$_2$C(R$^{22}$)$_2$, CR$^{21}$=CR$^{21}$, C≡C;

Y is C$_1$-C$_6$alkylene;

R$^1$ is selected from CN, C(=O)R$^{14}$, CO$_2$R$^{11}$, C(=O)NR$^{12}$R$^{13}$, C(=O)NR$^2$OR$^{22}$, OC(=O)R$^{11}$, OC(=O)NR$^{12}$R$^{13}$, NR$^{12}$R$^{13}$, NR$^{21}$NR$^{12}$R$^{13}$, NR$^{21}$C(=O)R$^{14}$, NR$^{21}$C(=O)NR$^{12}$R$^{13}$;

R$^2$ is selected from H, F, Cl, Br, I, OR$^{16}$, NR$^{17}$R$^{18}$, NHOH, NO$_2$, CN, CF$_3$, C$_1$-C$_6$ alkyl, C$_2$-C$_6$ alkenyl, C$_2$-C$_6$ alkynyl, C$_3$-C$_7$ cycloalkyl, C(=O)R$^{16}$, CO$_2$R$^{16}$, OC(=O)R$^{16}$, C(=O)NR$^{17}$R$^{18}$, NR$^{15}$C(=O)R$^{16}$, NR$^{15}$CO$_2$R$^{16}$, OC(=O)NR$^{17}$R$^{18}$, and NR$^{15}$C(=S)R$^{16}$;

alternatively, two R$^2$ groups may be combined to form a methylenedioxy group, an ethylenedioxy group, or a propylenedioxy group;

R$^{11}$ at each occurrence is independently selected from H, C$_1$-C$_6$ alkyl, C$_3$-C$_7$ cycloalkyl, C$_6$-C$_{10}$ aryl, arylalkyl; wherein said alkyl, aryl, arylalkyl groups are optionally substituted with one to three R$^{20}$ groups;

R$^{12}$ and R$^{13}$ at each occurrence are each independently selected from H, and C$_1$-C$_6$ alkyl, C$_6$-C$_{10}$ aryl, and NR$^{23}$R$^{24}$, or R$^{12}$ and R$^{13}$, together with the nitrogen to which they are attached, form a 3-7 membered heterocyclic ring;

wherein said alkyl and aryl groups and heterocyclic ring are optionally substituted with one to three R$^{20}$ groups;

R$^{14}$ at each occurrence is independently selected from C$_1$-C$_6$ alkyl, C$_6$-C$_{10}$ aryl, and arylalkyl; wherein said alkyl, aryl and arylalkyl groups are optionally substituted with one to three R$^{20}$ groups;

R$^{15}$ at each occurrence is independently selected from H, C$_1$-C$_6$ alkyl;

R$^{16}$ at each occurrence is independently selected from H, C$_1$-C$_6$ alkyl, and C$_6$-C$_{10}$ aryl; wherein said alkyl and aryl groups are optionally substituted with one to three R$^{20}$ groups;

R$^{17}$ and R$^{18}$ at each occurrence are each independently selected from H, C$_1$-C$_6$ alkyl, and C$_6$-C$_{10}$ aryl, or R$^{17}$ and R$^{18}$, together with the nitrogen to which they are attached, form a 3-7 membered heterocyclic ring;

wherein said alkyl and aryl groups and heterocyclic ring are optionally substituted with one to two oxo groups;

R$^{20}$ at each occurrence is independently selected from F, Cl, Br, I, OR$^{22}$, NR$^{23}$R$^{24}$, NHOH, NO$_2$, CN, CF$_3$, C$_1$-C$_6$ alkyl optionally substituted by one to three OH, C$_2$-C$_6$ alkenyl, C$_2$-C$_6$ alkynyl, C$_3$-C$_7$ cycloalkyl, 3-7 membered heterocycloalkyl, phenyl substituted by zero to one OR$^{26}$, 5 or 6 membered heteroaryl, arylalkyl, =O, C(=O)R$^{22}$, CO$_2$R$^{22}$, OC(=O)R$^{22}$, C(=O)NR$^{23}$R$^{24}$, NR$^{21}$C(=O)R$^{22}$, NR$^{21}$CO$_2$R$^{22}$, and OC(=O)NR$^{23}$R$^{24}$;

R$^{21}$ at each occurrence is independently selected from H and C$_1$-C$_6$ alkyl;

R$^{22}$ at each occurrence is independently selected from H, C$_1$-C$_6$ alkyl, C$_1$-C$_6$ alkyl-OH and C$_6$-C$_{10}$ aryl;

R$^{23}$ and R$^{24}$ at each occurrence are each independently selected from H, C$_1$-C$_6$ alkyl, and C$_6$-C$_{10}$ aryl, or R$^{23}$ and R$^{24}$, together with the nitrogen to which they are attached, form a 3-7 membered heterocyclic ring optionally substituted with one to three oxo groups;

R$^{25}$ at each occurrence is independently selected from H, F, Cl, Br, C$_1$-C$_6$ alkyl, C$_1$-C$_6$ and alkyloxy;

x is 1, 2, 3, or 4;

comprising the steps of:
a) contacting a pro-chiral sulphide of formula (IIb)

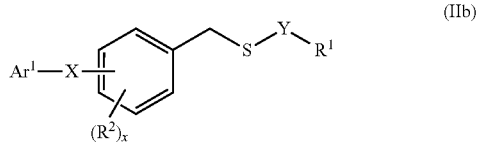

(IIb)

wherein Ar$^1$, X, Y, R$^1$, R$^2$ and x are as defined above, with a metal chiral ligand complex, a base and an oxidizing agent in an organic solvent; and optionally
b) isolating the obtained sulphoxide of formula (Ib).

In a preferred embodiment, the sulphoxide of formula (Ib) is a compound of formula (Ib) wherein:

Ar$^1$ is a C$_6$-C$_{10}$ aryl group substituted by 0-5 R$^3$ or 5 to 14 membered heteroaryl group substituted by 0-5 R$^3$, wherein said heteroaryl group comprises one, two, or three heteroatoms selected from N, O or S. Preferably, said C$_6$-C$_{10}$ aryl group is selected from phenyl, naphtyl and said 5 to 14 membered heteroaryl group is selected from phenoxathiinyl, pyrimidinyl, quinolinyl, isoxazolyl, thienyl, benzothienyl, (1,1-dioxo)-benzothienyl, indolyl, furyl, benzofuryl, pyridyl, seleninyl, 1,3-dihydro-isoindolyl, pyrrolyl, and 2-benzo[1,4]dioxine;

X is a bond, O, S(O)$_2$, NH, OCH$_2$, CH$_2$O, CH$_2$NH, NHCH, C(=O)NH, NHC(=O), S(O)$_2$NH, NHS(O)$_2$, CH$_2$CH$_2$, CH=CH, C≡C; and more preferably X is O, S(O)$_2$, NH, OCH$_2$, CH$_2$NH, S(O)$_2$NH;

In another preferred embodiment, the invention relates to a method for preparing a sulphoxide compound of formula (Ic) either as a single enantiomer or in an enantiomerically enriched form:

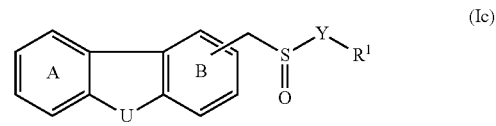

(Ic)

wherein:
U, is selected from a bond, CH$_2$, CR$^{23}$R$^{24}$, O, S(O)$_y$, NR$^{11}$, C(=O), CHOH, CHOR$^{14}$, C=NOR$^{14}$, or C=NNR$^{12}$R$^{13}$;

Rings A and B are optionally substituted with one to three groups selected from H, F, Cl, Br, I, OR$^{22}$, NR$^{23}$R$^{24}$, NHOH, NO$_2$, CN, CF$_3$, C$_1$-C$_6$ alkyl, C$_2$-C$_6$ alkenyl, C$_2$-C$_6$ alkynyl, C$_3$-C$_7$ cycloalkyl, 3-7 membered heterocycloalkyl, phenyl, 5 or 6 membered heteroaryl, arylalkyl, C(=O)R$^{22}$, CO$_2$R$^{22}$, OC(=O)R$^{22}$, C(=O)NR$^{23}$R$^{24}$, NR$^{21}$C(=O)R$^{22}$, NR$^{21}$CO$_2$R$^{22}$, and OC(=O)NR$^{23}$R$^{24}$;

Y is C$_1$-C$_6$alkylene;

R$^1$ is selected from CN, C(=O)R$^{14}$, CO$_2$R$^{11}$, C(=O)NR$^{12}$R$^{13}$, C(=O)NR$^{21}$OR$^{22}$, OC(=O)R$^{11}$, OC(=O)NR$^{12}$R$^{13}$, NR$^{12}$R$^{13}$, NR$^{21}$NR$^{12}$R$^{13}$, NR$^{21}$C(=O)R$^{14}$, NR$^{21}$C(=O)NR$^{12}$R$^{13}$;

R$^{11}$ at each occurrence is independently selected from H, C$_1$-C$_6$ alkyl, C$_3$-C$_7$ cycloalkyl, C$_6$-C$_{10}$ aryl, arylalkyl; wherein said alkyl, aryl, arylalkyl groups are optionally substituted with one to three R$^{20}$ groups;

R$^{12}$ and R$^{13}$ at each occurrence are each independently selected from H, C$_1$-C$_6$ alkyl, C$_6$-C$_{10}$ aryl, and NR$^{23}$R$^{24}$, or R$^{12}$ and R$^{13}$, together with the nitrogen to which they are attached, form a 3-7 membered heterocyclic ring;

wherein said alkyl and aryl groups and heterocyclic ring are optionally substituted with one to three R$^{20}$ groups;

R$^{14}$ at each occurrence is independently selected from C$_1$-C$_6$ alkyl, C$_6$-C$_{10}$ aryl, and arylalkyl; wherein said alkyl, aryl and arylalkyl groups are optionally substituted.

R$^{20}$ at each occurrence is independently selected from F, Cl, Br, I, OR$^{22}$, NR$^{23}$R$^{24}$, NHOH, NO$_2$, CN, CF$_3$, C$_1$-C$_6$ alkyl optionally substituted by one to three OH, C$_2$-C$_6$ alkenyl, C$_2$-C$_6$ alkynyl, C$_3$-C$_7$ cycloalkyl, 3-7 membered heterocycloalkyl, phenyl substituted by zero to one OR$^{25}$, 5 or 6 membered heteroaryl, arylalkyl, =O, C(=O)R$^{22}$, CO$_2$R$^{22}$, OC(=O)R$^{22}$, C(=O)NR$^{23}$R$^{24}$, NR$^{21}$C(=O)R$^{22}$, NR$^{21}$CO$_2$R$^{22}$, and OC(=O)NR$^{23}$R$^{24}$;

$R^{21}$ at each occurrence is independently selected from H and $C_1$-$C_6$ alkyl;

$R^{22}$ at each occurrence is independently selected from H, $C_1$-$C_6$ alkyl, $C_1$-$C_6$ alkyl-OH and $C_6$-$C_{10}$ aryl;

$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocyclic ring optionally substituted with one to three oxo groups;

$R^{25}$ at each occurrence is independently selected from H, F, Cl, Br, $C_1$-$C_6$ alkyl, $C_1$-$C_6$ and alkyloxy;

y is 0, 1 or 2 comprising the steps of:

a) contacting a pro-chiral sulphide of formula (IIc)

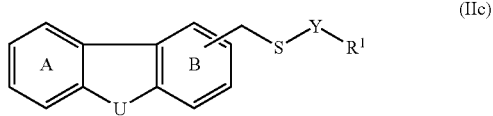

wherein U, Y and $R^1$ are as defined above, with a metal chiral ligand complex, a base and an oxidizing agent in an organic solvent; and optionally b) isolating the obtained sulphoxide of formula (Ic).

In a preferred embodiment, the sulphoxide prepared by the method is according to the invention is a sulphoxide of formula (Ic), wherein:

U, is selected from a bond, $CH_2$, O, $S(O)_y$, NH, C(=O), CHOH, $CHOCH_3$, C=NOH, or C=$NNH_2$; and more preferably, wherein U is a bond, $CH_2$, O, $S(O)_y$, NH, y is 0, 1 or 2.

In another preferred embodiment, the invention relates to a method for preparing a sulphoxide compound of formula (Id) either as a single enantiomer or in an enantiomerically enriched form:

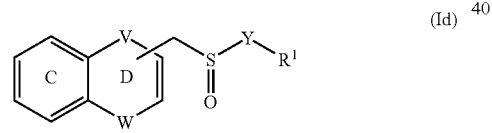

wherein:

V and W are independently selected from a bond, $CH_2$, $CR^{23}R^{24}$, O, $S(O)_y$, $NR^{11}$, C(=O), CHOH, $CHOR^{14}$, C=$NOR^{14}$, or C=$NNR^{12}R^{13}$;

Ring C is optionally substituted with one to three groups selected from H, F, Cl, Br, I, $OR^{22}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, C(=O)$R^{22}$, $CO_2R^{22}$, OC(=O)$R^{22}$, C(=O)$NR^{23}R^{24}$, $NR^{21}$C(=O)$R^{22}$, $NR^{21}CO_2R^{22}$, and OC(=O)$NR^{23}R^{24}$;

Ring D is optionally substituted with one group selected from $C_1$-$C_6$ alkyl, phenyl, and 5-10 membered heteroaryl;

Y is $C_1$-$C_6$alkylene;

$R^1$ is selected from CN, C(=O)$R^{14}$, $CO_2R^{11}$, C(=O)$NR^{12}R^{13}$, C(=O)$NR^{21}OR^{22}$, OC(=O)$R^{11}$, OC(=O)$NR^{12}R^{13}$, $NR^{12}R^{13}$, $NR^{21}NR^{12}R^{13}$, $NR^{21}$C(=O)$R^{14}$, $NR^{21}$C(=O)$NR^{12}R^{13}$;

$R^{11}$ at each occurrence is independently selected from H, $C_1$-$C_6$ alkyl, $C_3$-$C_7$ cycloalkyl, $C_6$-$C_{10}$ aryl, arylalkyl;

wherein said alkyl, aryl, arylalkyl groups are optionally substituted with one to three $R^{20}$ groups;

$R^{12}$ and $R^{13}$ at each occurrence are each independently selected from H, $C_1$-$C_6$ alkyl, $C_6$-$C_{10}$ aryl, and $NR^{23}R^{24}$, or $R^{12}$ and $R^{13}$, together with the nitrogen to which they are attached, form a 3-7 membered heterocyclic ring;

wherein said alkyl and aryl groups and heterocyclic ring are optionally substituted with one to three $R^{20}$ groups;

$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted.

$R^{20}$ at each occurrence is independently selected from F, Cl, Br, I, $OR^{22}$, $NR^{23}R^{24}$, NHOH, $NO_2$, CN, $CF_3$, $C_1$-$C_6$ alkyl optionally substituted by one to three OH, $C_2$-$C_6$ alkenyl, $C_2$-$C_6$ alkynyl, $C_3$-$C_7$ cycloalkyl, 3-7 membered heterocycloalkyl, phenyl substituted by zero to one $OR^{25}$, 5 or 6 membered heteroaryl, arylalkyl, =O, C(=O)$R^{22}$, $CO_2R^{22}$, OC(=O)$R^{22}$, C(=O)$NR^{23}R^{24}$, $NR^{21}$C(=O)$R^{22}$, $NR^{21}CO_2R^{22}$, and OC(=O)$NR^{23}R^{24}$;

$R^{21}$ at each occurrence is independently selected from H and $C_1$-$C_6$ alkyl;

$R^{22}$ at each occurrence is independently selected from H, $C_1$-$C_6$ alkyl, $C_1$-$C_6$ alkyl-OH and $C_6$-$C_{10}$ aryl;

$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocyclic ring optionally substituted with 5 at each occurrence is independently selected from H, F, Cl, Br, $C_1$-$C_6$ alkyl, $C_1$-$C_6$ and alkyloxy;

y is 0, 1 or 2;

comprising the steps of:

a) contacting a pro-chiral sulphide of formula (IId)

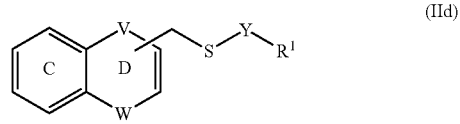

wherein V, W, Y and $R^1$ are as defined above, with a metal chiral ligand complex, a base and an oxidizing agent in an organic solvent; and optionally b) isolating the obtained sulphoxide of formula (Ib).

In a preferred embodiment, the sulphoxide is a compound of formula (Id), wherein:

V and W are independently selected from a bond, $CH_2$, O, NH, C(=O), CHOH, $CHOCH_3$, C=$NOCH_3$, or C=$NNH_2$, and ring D substituted by a phenyl; and more preferably W is a bond and V selected from O, NH, S and ring D substituted by a phenyl.

More preferably, $R^1$ is selected from CN, C(=O)$R^{14}$, $CO_2R^{11}$, C(=O)$NR^{12}R^{13}$, C(=O)$NR^{21}OR^{22}$ and $NR^{12}R^{13}$.

Most preferably, $R^1$ is selected from CN, $CO_2R^{11}$, C(=O)$NH_2$, or C(=O)NHOH.

Preferably, the $R^{11}$ group is H, alkyl or arylalkyl including notably methyl, ethyl, isopropyl, benzyl, and tolyl.

Preferably, Y is $CH_2$ or $CH_2CH_2$, more preferably Y is $CH_2$.

Preferably, the sulphoxide compounds prepared according to the method of the invention are sulphoxides of formula (Ia) and (Ib).

When the sulphoxide is a compound of formula (Ib), X is preferably O.

Preferably, $Ar^1$ is a $C_6$-$C_{10}$ aryl group, most preferably a phenyl group, optionally substituted by one to three $R^3$ groups.

Preferably, $R^3$ groups are F, Cl, Br, I, notably Cl.

In a particular embodiment, $Ar^1$ is substituted by one or two $R^3$ groups, one of them being preferably located in para on the phenyl ring.

Thus, $Ar^1$ groups are notably selected from phenyl, 4-chlorophenyl and 3,4-dichlorophenyl groups.

Preferably, $Ar^1$ or $Ar^1$—X are located in ortho position on the phenyl ring E.

Most preferably, the sulphoxide prepared by the method according to the invention are those wherein:

the sulphoxide of formula (Ia), wherein $Ar^1$ is a 4-chlorophenyl in ortho position on ring E, $R^2$ is H, Y is $CH_2$, $R^1$ is —C(=O)$NH_2$, called (−) or (+)-2-[2-(4-chlorophenyl)benzyl]sulphinylacetamide;

the sulphoxide of formula (Ia), wherein $Ar^1$ is phenyl in ortho position on ring E, $R^2$ is H, Y is $CH_2$, $R^1$ is —C(=O)$NH_2$, called (−) or (+)2-[([1,1'-biphenyl]-2-ylmethyl)sulphinyl]acetamide;

the sulphoxide of formula (Ib), wherein $Ar^1$ is 3,4-dichlorophenyl, X is O, the $Ar^1$—X— group being in ortho position on ring E, $R^2$ is H, Y is $CH_2$, $R^1$ is —C(=O)$NH_2$, called (−) or (+)2-[2-(3,4-dichlorophenoxy)-benzyl]sulphinyl acetamide, as well as their corresponding acids ($R^1$=$CO_2H$) and esters ($R^1$=$CO_2R^{11}$).

Step a)

The oxidation reaction is carried out in an organic solvent. Surprisingly, the solvent is not as essential for the enantioselectivity of the oxidation, according to the invention. The solvent may hence be chosen with respect to suitable conditions from an industrial point of view, as well as environmental aspects. Suitable organic solvents are notably toluene, ethyl acetate, tetrahydrofuran, acetonitrile, acetone and methylene chloride and can be readily determined by one skilled in the art. From an environmental point of view, non-chlorinated solvents are preferred. In this regard, ethyl acetate and toluene are particularly preferred.

Preparation of the Metal Chiral Ligand Complex

The metal chiral ligand complex is prepared from a chiral ligand and a metal compound.

The metal compound is preferably a titanium, a zirconium, a vanadium or a manganese compound and more preferably a titanium compound.

Thus, preferred metal chiral ligand complexes are notably titanium, zirconium, vanadium or manganese chiral ligand complexes, more preferably a titanium chiral ligand complex.

The titanium compound is generally a titanium (IV) compound, preferably a titanium (IV) alkoxide, such as, in particular, titanium (IV) isopropoxide or propoxide.

The chiral ligand is a chiral compound capable of reacting with the titanium compound. Such compounds are preferably chosen from hydroxy substituted compounds, preferably having more than one hydroxy group. Thus, the chiral ligand is preferably a chiral alcohol, such as a $C_2$-symmetric chiral diol or a $C_3$-symmetric chiral triol. The chiral alcohol may be branched or unbranched alkyl alcohol, or an aromatic alcohol.

Preferred chiral ligands are binaphtol, mandelic acid, hydrobenzoin, esters of tartaric acid, such as (+)-dialkyl-L-tartrate or (−)-dialkyl-D-tartrate, preferably (+)-di($C_1$-$C_4$) alkyl-L-tartrate or (−)-di($C_1$-$C_4$)alkyl-D-tartrate, notably (+)-dimethyl-L-tartrate or (−)-dimethyl-D-tartrate, (+)-diethyl-L-tartrate or (−)-diethyl-D-tartrate, (+)-diisopropyl-L-tartrate or (−)-diisopropyl-D-tartrate, (+)-dibutyl-L-tartrate or (−)-dibutyl-D-tartrate and (+)-ditertbutyl-L-tartrate or (−)-ditertbutyl-D-tartrate. Especially preferred are (+)-diethyl-L-tartrate and (−)-diethyl-D-tartrate.

Preferred chiral ligands also include $C_3$-symmetric trialkanolamines, notably of formula (1):

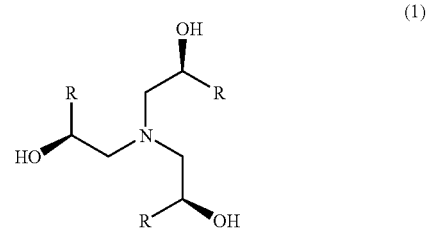

(1)

wherein R is a lower alkyl or aryl, as for example methyl, t-butyl and phenyl. Preferred chiral ligands also include Schiff base of general formula (2a) or (2b):

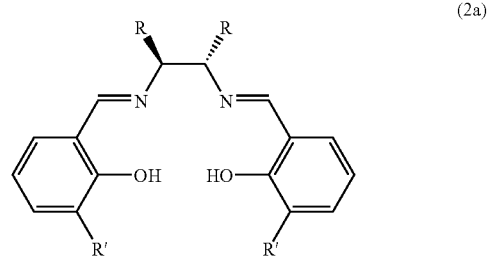

(2a)

wherein R is the same and represents a lower alkyl or aryl, such as methyl or phenyl, or are attached together to form a cycloalkyl group such as cyclohexyl; R' is a lower alkyl or alkoxy;

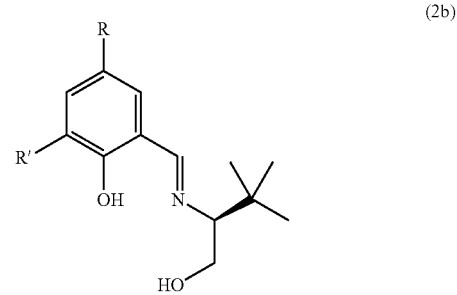

(2b)

wherein R is a lower alkyl or $NO_2$;
R' is a lower alkyl or alkoxy.

These Schiff bases may form a chiral ligand complex with the metal, known as chiral (salen)-metal complex.

Preferred examples of metal chiral ligand complexes are $C_2$-symmetric diols or $C_3$-symmetric trialkanolamine titanium (IV) complexes, $C_3$-symmetric trialkanolamine zirconium (IV) complexes, chiral (salen) manganese (III) complexes, chiral (salen) vanadium (IV) complexes, notably those disclosed in Fernandez et al., Chem. Rev. 2003; 103(9): 3651-3706.

Especially preferred metal chiral ligand complexes are titanium chiral diol complexes and most preferably diethyl tartrate titanium (IV) complexes.

The stoichiometry of the metal chiral ligand complex may vary and is not critical for the invention.

In particular, the ratio of the chiral ligand with respect to the metal compound may vary from 1 to 4 equivalents and is preferably 2 equivalents.

In accordance with a preferred aspect of the invention, the preparation of the metal chiral complex further comprises water. Indeed, it has been found that the presence of water in the metal chiral ligand complex further improves the enantioselectivity of the reaction.

The amount of water involved in the metal chiral ligand complex may vary from 0.1 to 1 equivalent with respect to the titanium compound. In an especially preferred embodiment, the amount of water ranges from 0.4 to 0.8 equivalent with respect to the metal compound.

Thus it is not necessary to pre-dry the reactants. According to another particular embodiment, the water present in the reaction mixture coming only from the residual humidity of the reactants may be sufficient.

The amount of the metal chiral ligand complex used in the process is not critical. It has however been found advantageous to use less than 0.50 equivalent with respect to the pro-chiral sulphide, especially 0.05-0.30 equivalent, and most preferably 0.1-0.30 equivalent. Surprisingly, even very low amounts of complex, such as for instance 0.05 equivalent may be used in the process according to the invention with excellent results.

The metal chiral ligand complex may be prepared in the presence of the pro-chiral sulphide or before the pro-chiral sulphide is added to the reaction vessel.

According to one preferred embodiment, the preparation of the metal chiral ligand complex is performed in the presence of the pro-chiral sulphide, i.e. the pro-chiral sulphide is loaded into the reaction vessel before the components used for the preparation of the chiral complex are introduced.

The reaction time for the formation of the metal chiral ligand complex depends on the temperature.

Indeed, it has been found that the reaction kinetics of the metal chiral ligand complex appear to depend on the couple temperature and reaction time. Thus, the higher the temperature, the lower the reaction time is. Inversely, the lower the temperature, the longer the reaction time is.

As an example, at an elevated temperature, which as used herein means a temperature between 20-70° C., preferably of about 40-60° C., most preferably of about 50-55° C., less than two hours are generally sufficient to form the metal chiral ligand complex. As an example, at 55° C., the metal chiral ligand complex may be formed in about 50 minutes. At a lower temperature, such as at 25° C., the metal chiral ligand complex may be formed in about 24 hours.

Introduction of a Base

The asymmetric oxidation according to the invention is carried out in the presence of a base.

Indeed, the enantioselectivity of the reaction is surprisingly enhanced when a base is present during oxidation. Enantioselectivities of more than 99% may be thus observed. The order of introduction of the base is not critical, provided that it is added before the oxidizing agent. The base may be introduced before or after the pro-chiral sulphide and, preferably after the metal chiral ligand complex is formed.

Preferably, the base is introduced after the metal chiral ligand complex is formed, and after the pro-chiral sulphide is added.

In another preferred embodiment, the base is contacted with the metal chiral ligand complex and the pro-chiral sulphide for few minutes, preferably for at least 3 minutes before adding the oxidant in order to increase the enantioselectivity.

According to a preferred embodiment of the invention, the base is introduced at the temperature at which the oxidation reaction is carried out, hereafter called "oxidation temperature".

The base should be soluble in the reaction mixture. Preferably, it is an organic base, such as for instance an amine. Especially suitable bases are amines, preferably tertiary amines, such as triethylamine, N,N-diisopropyl-ethylamine, dimethyl-ethanolamine, triethanolamine and, most preferably, N,N-diisopropyl-ethylamine and triethylamine.

The amount of base added to the reaction mixture should not exceed a certain value, because it may affect the enantioselectivity of the reaction. In particular, an amount of less than 2 equivalents, notably of 0.5 equivalent with respect to pro-chiral sulphide, especially 0.01 to 2 equivalents, preferably of 0.05 to 0.5 equivalent and most preferably of 0.1 to 0.3 equivalent, has proven to be advantageous.

Oxidation

Surprisingly, the process does not require very low temperatures such as −20° C., as described by Kagan and co-workers as essential to obtain a good enantioselectivity. This feature is particularly interesting since such low temperatures result in long reaction times.

The temperature will however be chosen such as to avoid decomposition of the reactants and excessive reaction times.

In a preferred embodiment, the oxidizing agent is contacted with the sulphide, the metal chiral ligand complex and the base at a temperature between 0-60° C., preferably 15-40° C. and more preferably at room temperature, that is between about 20-25° C.

A suitable oxidizing agent for the asymmetric oxidation may be a hydroperoxide, preferably hydrogen peroxide, tert-butylhydroperoxide or cumene hydroperoxide, and most preferably the latter.

The oxidizing agent is left in contact with the other reactants during a sufficient period to achieve satisfactory conversion rate, but not too long in order not to affect the purity and the enantioselectivity of the product obtained.

In a preferred embodiment, the oxidizing agent is left in contact with the other reactants during about 30 minutes to 3 hours.

The amount of the oxidizing agent is not critical with respect to the enantioselectivity of the reaction. However, an excessive amount of oxidizing agent may affect the purity of the product obtained by favoring the formation of sulphone.

An amount of oxidizing agent of less than 2 equivalents relative to the amount of sulphide amide is generally preferred and an especially preferred amount is 0.8 to 1.2 equivalents and more preferably 1.0 equivalent.

Step b)

The sulphoxide formed during the oxidation reaction may be isolated according to conventional procedures.

Thus, as described in the literature, the reaction mixture may be treated with water or an aqueous sodium hydroxide solution, which results in the formation of a gel containing metal salts. This gel may be filtered off and thoroughly washed with an organic solvent. The filtrate may be extracted with an organic solvent. It may also be crystallized in an organic or aqueous solvent to obtain the desired enantiomer.

According to an advantageous aspect of the invention, the obtained sulphoxide forms a precipitate that can be directly isolated by filtration and optionally washed with water or an organic solvent such as ethyl acetate, toluene, ethanol, methylene chloride. Advantageously, the precipitate is a crystalline and highly pure form. Thus, advantageously, the method avoids cumbersome subsequent treatments mentioned above.

Step c)

In accordance with a preferred embodiment, the method further comprises a step c) of crystallization of the isolated product obtained in step b).

Such crystallization step may be useful to improve the purity of the isolated product and/or to produce a desired polymorphic form and/or to improve the enantiomeric excess of the targeted enantiomer and/or to obtain lots with a specific particle size.

The crystallization may be carried out in organic solvents optionally in admixture with water. Suitable organic solvent are notably alcohols, ketones, esters, ethers, chlorinated solvents, polar and aprotic solvents and mixtures thereof, or mixture with water.

Examples of alcohols include methanol, ethanol, propanol, isopropyl alcohol, tert-butanol, 2-methyl-1-butanol, benzyl alcohol.

Among the chlorinated solvents, dichloromethane may be mentioned.

Among the ketones, acetone, methylethylketone, 2-pentanone, cyclo-hexanone may be mentioned.

Among the ethers, tetrahydrofuran, dioxane, may be mentioned.

Other suitable solvents can be readily determined by one skilled in the art.

Surprisingly, it has been found that the presence of water in the crystallization solvent allows to reach an enhanced enantiomeric excess and purity. In addition, a crystallization step using an organic solvent/water mixture advantageously allows to reduce the volume of organic solvent utilized in the process.

Thus, preferred crystallization solvents are alcoholic solvents, and mixtures of organic solvents with water, more preferred are mixtures of organic solvents with water, most preferred are organic solvent mixed with up to 40% water. Are particularly preferred mixtures of organic solvents with up to 25% of water.

The product obtained in step b) if needed may also further be enantiomerically enriched. Such methods are known in the art and include notably preferential crystallization.

Thus, in a particular embodiment of the invention, the method further comprises a step of preferential crystallization for improving the enantiomeric excess.

Such a method of optical resolution by preferential crystallization of (±) modafinic acid has been disclosed in the French patent application WO 2004/060858.

Advantageously, the sulphoxide compound of formula (I) is obtained with an enantiomeric excess of at least 80%, more preferably of at least 95% and most preferably of at least 99%, notably at the end of step b).

The obtained enantiomer may further be processed to produce lots with a specific particle size. Conventional methods as milling, sieving, micronization, comminution, separation by weight or by density are known by those skilled in the art.

The enantiomers of the sulphoxide compounds of formula (I) or (Ia), (Ib), (Ic), and (Id) wherein $R^1$ is —C(=O)OR$^{11}$, acids or esters, may be converted into their corresponding amide, that is a sulphoxide compound of formula (I) or (Ia), (Ib), (Ic), and (Id) wherein $R^1$ is —C(=O)NH$_2$.

The enantiomers of arylmethanesulphinyl acetic acid or the ester thereof obtained by the above method may further be converted into the corresponding amide that is arylmethanesulphinyl acetamide enantiomers.

Thus, in accordance with a particular embodiment, esters of arylmethanesulphinyl acetic acid enantiomers may be converted into the corresponding arylmethanesulphinyl acetamide enantiomers by an amidation reaction, notably with ammonia.

Hence, arylmethanesulphinyl acetic acid may be converted into arylmethanesulphinyl acetamide by:
  esterification of the carboxylic acid function by any suitable method such as, for example, by reaction with a lower alkyl alcohol, in presence of dimethylsulfate. The obtained corresponding ester may then be transformed by
  amidation of the resulting ester by any suitable method, notably in presence of ammonia.

Such methods have been disclosed notably in U.S. Pat. No. 4,927,855 for modafinil.

In accordance with another particular embodiment, the enantiomers of the sulphoxide compounds of formula (I) or (Ia), (Ib), (Ic), and (Id) wherein $R^1$ is CN may be converted into their corresponding amide, that is a sulphoxide compound of formula (I) or (Ia), (Ib), (Ic), and (Id) wherein $R^1$ is —C(=O)NH$_2$.

This conversion may be realized by any suitable method known in the art. Examples of such suitable methods are notably oxidation or hydrolysis of the nitrile group, for instance, by catalytic phase transfer with peroxides or by basic or acid hydrolysis with an appropriate inorganic base or acid in mild experimental conditions.

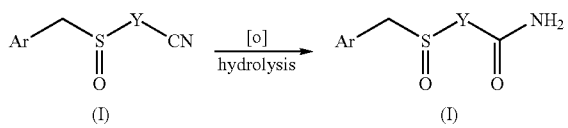

Thus, the desired enantiomer of an arylmethanesulphinyl acetamide may be prepared from the appropriate arylmethanesulphinyl acetonitrile enantiomers, for example by oxidation with hydrogen peroxide in the presence of tetrabutylammonium hydrogen sulfate in alkaline conditions or also by direct basic or acidic hydrolysis.

In accordance with another embodiment, the method according to the invention implements a sulphide of formula (II) or (IIa), (IIb), (IIc), (IId), wherein $R^1$ is —C(=O)NHOH, which may be prepared according to any suitable method known in the art and notably to the method disclosed in U.S. Pat. No. 4,098,824.

In accordance with another embodiment, the method according to the invention implements a sulphide of formula (II) or (IIa), (IIb), (IIc), (IId), wherein $R^1$ is —C(=O)NH$_2$.

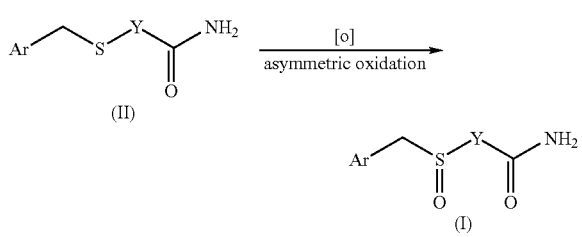

Sulphides of formula (II) or (IIa), (IIb), (IIc), (IId) may be prepared by any suitable method known in the art.

EXAMPLES

Material and Methods

For each sulphide compound, experimental conditions for the determination of the enantiomeric excess or the chemical purity have to be set up by appropriate chromatographic methods known in the art.

Examples of method developed are as follows:

Determination of the Enantiomeric Excess

The enantiomeric excess value gives an indication of the relative amounts of each enantiomer obtained. The value was defined as the difference between the relative percentages for the two enantiomers.

As an example, the enantiomeric composition of the obtained sulphoxide has been determined by chiral High Performance Liquid Chromatography (HPLC) under the following conditions:

Column: AGP (150×4.0 mm; 5 µm)
Oven temperature: 25° C.
Flow: 0.8 m/min
Wavelength: DAD λ=230 nm
As examples:
Eluent: ammonium acetate 5 mM/absolute ethanol (82.5/17.5 v/v)
The retention times for the (+) and (−)2-[2-(4-chlorophenyl)benzyl]sulphinyl acetamide were 4.4 min and 6.8 min, respectively.
Eluent: ammonium acetate 20 mM pH5 (acetic acid conc.)+7.5% n-propanol
The retention times of the enantiomers of 2-[2-(4-chlorophenyl)benzyl]sulphinyl acetic acid were 6.8 min and 9.7 min, respectively.

or,
Column: chiralcel AD-H (150×4.6 mm; 5 µm)
Oven temperature: 25° C.
Eluent: n-heptane/absolute ethanol 70/30 (v/v)
Flow: 1.0 ml/min
Wavelength: DAD λ=220 nm
As an example:
The retention times of methyl 2-[2-(4-chlorophenyl)benzyl]sulphinyl acetate enantiomers were 7.2 min and 9.2 min, respectively,
or,
Column: AGP-Chiral (150×4 mm; 5 µm)
Oven temperature: 30° C.
Eluent: 0.5% (v/v) pentan-1-ol/ammonium acetate 20 mM
Flow: 0.8 ml/min
Wavelength: DAD λ=230 nm
As an example:
The retention times of the (+) and (−)2-[([1,1'-biphenyl]-2-ylmethyl)sulphinyl]acetamide enantiomers were 6.8 min and 8.1 min, respectively.

Determination of the Chemical Purity in the Examples

The purity value in examples was defined as the ratio of the amount of enantiomers obtained after isolation with respect to the total amount of products present. Studied impurities measured were mainly the unchanged parent compound (pro-chiral sulphide) and the sulphone resulting from an over oxidation during the process, potential degradation products, intermediates of the synthesis of the pro-chiral sulphide.

As an example, the purity of the obtained sulphoxides has been determined by High Performance Liquid Chromatography (HPLC) under the following conditions:

Column: Zorbax Eclipse XDB C8 (150×4.6 mm; 5 µm)
Oven temperature: 25° C.
Eluent: A=water+0.1% trifluoroacetic acid
B=acetonitrile+0.1% trifluoroacetic acid with a gradient of 90% A to 100% B in 20 minutes
Flow: 1 ml/min
Wavelength: DAD λ=220 nm
As examples:
Retention time for the 2-[2-(4-chlorophenyl)benzyl]sulphinyl]acetic acid: 11.0 min.
Retention time for the 2-[2-(4-chlorophenyl)benzyl]sulphonyl]acetic acid:12.5 min.
Retention time for the 2-[2-(4-chlorophenyl)benzyl]sulphanyl]acetic acid:14.4 min.

or

Retention time for the 2-[2-(4-chlorophenyl)benzyl]sulphinyl]acetamide: 10.0 min.
Retention time for the 2-[2-(4-chlorophenyl)benzyl]sulphonyl]acetamide: 11.6 min.
Retention time for the 2-[2-(4-chlorophenyl)benzyl]sulphanyl]acetamide:12.9 min.

or

Retention time for the methyl 2-[2-(4-chlorophenyl)benzyl]sulphinyl]acetate: 12.8 min.
Retention time for the methyl 2-[2-(4-chlorophenyl)benzyl]sulphonyl]acetate: 14.5 min.
Retention time for the methyl 2-[2-(4-chlorophenyl)benzyl]sulphanyl]acetate: 16.9 min.

Example 1

Asymmetric synthesis of (−)-2-[2-(4-chlorophenyl)benzyl]sulphinylacetamide

A solution of (S,S)-(−)-diethyl-tartrate (2.47 g; 0.012 mol; 0.4 eq.) in a solvent (3.5 vol. vs thioacetamide) was introduced in a reactor with an impeller, containing 6.5 vol (vs thioacetamide) of the same solvent. The solution was stirred and heated to 50° C. before adding 0.2 equivalent of titanium (IV) tetraisopropoxide (1.71 g; 1.77 mL; 0.006 mol; 0.2 eq) and water (QSP to achieve 0.095 eq. in the mixture) and kept stirring at 50° C. for one hour. In these conditions, the resulting chiral titanium complex had the stoichiometry of DET/Ti(OiPr)$_4$/H$_2$O: 2/1/0.475 and corresponded to 0.2 eq. with respect to the thioacetamide. After stirring at 50° C. for one hour, 1.0 eq. (8.75 g; 0.03 mol) of 2-[2-(4-chlorophenyl)benzyl]sulphanyl acetamide was added and contacted for 30 min. After cooling to 20° C., were successively added 0.2 eq. (0.61 g; 0.84 mL; 0.006 mol) of triethylamine and around 10 minutes later, 1.0 eq (4.57 g; 5.0 mL; 0.03 mol) of cumene hydroperoxide within less than 5 minutes.

After contacting for an appropriate time period, the formed precipitate was isolated by filtration, washed and dried under vacuum.

As reported in table 1, experiments were performed in various solvents, the experimental conditions being the same as in the above general procedure.

TABLE 1

| Entry | Solvent | E.e. (%) | Purity (%) | Yield (%) |
|---|---|---|---|---|
| 1 | Ethyl acetate | 85 | – | 85.1 |
| 2 | Dichloromethane | 86.7 | – | 77.7 |
| 3 | Acetonitrile | 98.1 | – | 72.6 |
| 4 | Tetrahydrofuran | 96.1 | 97.4 +0.9% sulphone, +0.6% sulphanyl | 56.9 |

E.e. = enantiomeric excess

In both experiments, the sulphoxide amide was obtained with a high enantioselectivity (E.e. equal or superior to 85%). A high purity (purity equal or superior to 97.4%) was obtained with tetrahydrofuran used as the solvent in the experimental conditions described above.

Example 2

Treatment of the Reaction Mixture as to Obtain the Required Enantiomer

When a precipitate was observed in the reaction mixture, the stirring rate was increased. After an appropriate precipitation time period, the precipitate was filtered, washed and dried under vacuum at about 30° C.

In the absence of precipitation, the kinetics of the oxidation reaction and of the enantioselectivity were recorded with time using the appropriate HPLC is methods. At the end of reaction period separation techniques well known in the art are used (as for example: liquid-liquid extraction, salt formation techniques . . . ) to extract the reaction end product.

As an example:

No direct precipitate was formed by asymmetric oxidation of the 2-[2-(4-chlorophenyl)benzyl]sulphanyl acetic acid. At the end of the reaction, the mixture was extracted with a potassium carbonate aqueous solution (0.6 M). The aqueous layers were washed with ethyl acetate and acidified by HCl (4N). The obtained precipitate was filtered, washed with water and dried under vacuum at 35° C.

Example 3

Asymmetric synthesis of (−) or (+)2-[([1,1'-biphenyl]-2-ylmethyl)sulphinyl]acetamide A solution of diethyl-tartrate [(S,S)-(−)DET] or [(R,R)-(+) DET] (2.47 g; 0.012 mol; 0.4 eq) in ethyl acetate (27 mL) was added to a suspension of 2-[([1,1'-biphenyl]-2-ylmethyl)sulphanyl]acetamide (7.70 g; 0.03 mol; 1.0 eq) in ethyl acetate (50 mL) at room temperature under stirring. The mixture was heated to 50° C. in an oil bath, under stirring, until complete dissolution. Then, 0.2 equivalent of titanium (IV) tetraisopropoxide (1.71 g; 1.77 mL; 0.006 mol; 0.02 eq.) and water (26 µL taking into account the sum of water present in reagents and solvent already introduced) were added, successively. In these conditions, the resulting chiral titanium complex had the stoichiometry of DET/Ti(OiPr)$_4$/H$_2$O: 2/1/0.5, and corresponded to 0.2 equivalent with respect to the thioacetamide. Stirring was maintained at 50° C. for at least 50 minutes.

The mixture was cooled to room temperature (21-23° C.) and triethylamine (0.61 g; 0.83 mL; 0.006 mol; 0.2 eq.) and cumene hydroperoxide (4.56 g; 5.0 mL; 0.03 mol; 1.0 eq.) were added, successively.

After contacting during about two hours under stirring, the formed precipitate was isolated by filtration and washed with ethyl acetate. After drying under vacuum for two days, the (−) or (+)-2-[([1,1'-biphenyl]-2-ylmethyl)sulphinyl]acetamide depending on the chiral ligand were obtained with a yield of 92.8% and 94%, respectively.

Results obtained are reported in table 2.

TABLE 2

| Entry | Chiral ligand | E.e. (%) | Purity (%) | Yield (%) |
|---|---|---|---|---|
| 1 | (S,S)-(−)-diethyl-tartrate | 94.0 | 97.3 | 92.8 |
| 2 | (R,R)-(+)-diethyl-tartrate | 96 | 98.0 | 94 |

E.e. = enantiomeric excess

In the experimental conditions described, both enantiomers were selectively obtained with a high enantioselectivity (superior or equal to 94%), high purity (superior or equal to 97.3%) and high yield (superior or equal to 92.8%) when using (S,S)-(−)-diethyl-tartrate or the (R,R)-(+)-diethyl-tartrate as chiral ligands.

Example 4

Asymmetric synthesis of (−) or (+)2-[2-(3,4-dichlorophenoxy)-benzyl]sulphinyl acetamide Protocol 1

To a solution of 2-[2-(3,4-dichlorophenoxy)-benzyl]sulphanyl acetamide (12 g; 0.035 mol; 1.0 eq) in a solvent (70 mL) heated to 40° C. until complete dissolution, a solution of diethyl-tartrate (2.89 g; 0.014 mol; 0.4 eq.) in the same solvent (50 mL) was added and the mixture was heated to 50° C. under stirring. Then, 0.2 equivalent of titanium (IV) tetraisopropoxide (1.99 g; 2.07 mL; 0.007 mol) and water (21.85 µL taking into account the sum of water present in reagents and solvent already introduced to obtain 0.003 mol, 0.095 eq. in the reaction mixture) were added successively 10 minutes apart. In these conditions, the resulting chiral titanium complex had the stoichiometry of DET/Ti(OiPr)$_4$/H$_2$O: 2/1/0.475 and corresponded to 0.2 equivalent with respect to the thioacetamide starting material. Stirring of the reaction mixture was maintained 1 hour at 50° C.

The mixture was slowly cooled to room temperature (25° C.) in a water bath, and triethylamine (0.707 g; 0.97 mL; 0.007 mol; 0.2 eq) was added. After about 10 minutes under stirring, 1.05 equivalents of cumene hydroperoxide 88% (6.35 g; 6.1 mL; 0.037 mol) were added.

After contacting during about 1 hour under stirring, the formed precipitate was isolated by filtration and washed with ethyl acetate.

Protocol 2

To a solution of diethyl-tartrate (2.89 g; 0.014 mol; 0.4 eq.) in a solvent (120 mL) heated to 50° C., 0.2 equivalent of titanium (IV) tetraisopropoxide (1.99 g; 2.07 mL; 0.007 mol) and water (23.03 µL taking into account the sum of water present in reagents and solvent already introduced to obtain 0.003 mol; 0.095 eq. in the reaction mixture) were added successively 5 minutes apart. In these conditions, the resulting chiral titanium complex had the stoichiometry of DET/Ti (OiPr)$_4$/H$_2$O: 2/1/0.475 and corresponded to 0.2 equivalent with respect to the sulphanyl acetamide starting material.

Stirring of the reaction mixture was maintained 1 hour at 50° C. Then, the 2-[2-(3,4-dichlorophenoxy)-benzyl]sulphanyl acetamide (12 g; 0.035 mol; 1.0 eq) was added and the mixture stirred 15 min at 50° C.

The mixture was slowly cooled (25-27° C.) in a water bath, and 0.2 equivalent of triethylamine (0.707 g; 0.975 mL; 0.007 mol) added. After about 10 minutes under stirring, 1.05 equivalents of cumene hydroperoxide 88% (6.39 g; 6.1 mL; 0.037 mol) were added. The resulting (−) or (+) sulphoxide began to precipitate. After contacting for about 1 hour and a half under stirring, the formed precipitate was isolated by filtration.

Results of four different experiments are reported in table 3.

TABLE 3

| Entry | Chiral ligand | Reagents introduction order | Solvent | E.e. (%) |
|---|---|---|---|---|
| 1 | (S,S)-(−)-DET | 1- Sulphide<br>2- (−) DET<br>3- Ti(OiPr)$_4$<br>4- H$_2$O<br>5- Et$_3$N<br>6- CHP | Ethyl acetate | 72 |
| 2 | (S,S)-(−)-DET | 1- (−) DET<br>2- Ti(OiPr)$_4$<br>3- H$_2$O<br>4- Sulphide<br>5- Et$_3$N<br>6- CHP | Ethyl acetate | 79 |
| 3 | (R,R)-(+)-DET | 1- (+) DET<br>2- Ti(OiPr)$_4$<br>3- H$_2$O<br>4- Sulphide<br>5- Et$_3$N<br>6- CHP | Toluene | 74 |
| 4 | (R,R)-(+)-DET | 1- Sulphide<br>2- (+) DET<br>3- Ti(OiPr)$_4$<br>4- H$_2$O<br>5- Et$_3$N<br>6- CHP | Ethyl acetate | 79 |

E.e. = enantiomeric excess; DET = Diethyl tartrate; Et$_3$N = triethylamine; CHP = Cumene hydroperoxide The reagents introduction order and solvents or the chiral ligand used influenced only slightly the enantioselectivity (72-79% range) of the asymmetric oxidation of the sulphide amide studied, provided that the triethylamine was added before the oxidant.

Additional crystallization steps in ethyl acetate lead to (−) or (+) 2-[2-(3,4-dichlorophenoxy)-benzyl]sulphinyl acetamide with >98% enantiomeric excess and > to 99.5% chemical purity.

Example 5

Example 5 corresponds to an example of optional re-worked processes that may be applied to the crystallized end product resulting from the asymmetric oxidation and isolated by filtration in order either to obtain an enantiomerically enriched form of the targeted enantiomer and/or to achieve a higher degree of purity by removing impurities as, as example, the initial pro-chiral sulphide and/or the sulphone.

A suspension of (−)-2-[2-(4-chlorophenyl)benzyl]sulphinylacetamide enantiomerically enriched (3.0 g; 0.010 mole) and solvent (5 volumes) was refluxed under stirring. If the sulphinylacetamide solubilization is incomplete, the appropriate volume of solvent is added to solubilize the starting material. After stirring for 30 minutes, the solution was cooled to room temperature (25° C.) and then kept at 15° C. in a water bath for 5 minutes. The precipitate was filtrated under vacuum, washed with cold solvent and dried under vacuum at 30° C. Results are reported in tables 4 and 5.

TABLE 4

| Entry | Solvent | Initial E.e. (%) | Final E.e. (%) | Yield (%) |
|---|---|---|---|---|
| 1 | EtOH/H$_2$O 95/5 (10 Vol) | 96.0 | 99.0 | 68.0 |
| 2 | EtOH/H$_2$O 95/5 (8 Vol) | 96.0 | 99.3 | 75.2 |

TABLE 5

| | Initial | | | Final | | |
|---|---|---|---|---|---|---|
| Entry | Purity (%) | Sulphide amide (%) | Sulphone amide (%) | Purity (%) | Sulphide amide (%) | Sulphone amide (%) |
| 1 | 97.1 | 0.6 | 0.9 | 98.3 | 0.2 | 0.9 |
| 2 | 97.1 | 0.6 | 0.9 | 98.4 | 0.15 | 0.9 |

In the above described experimental conditions, the crystallization step increased the purity level of the obtained sulphoxide and decreased by about 70% the percentage of the sulphide amide initially present.

The invention claimed is:

1. A compound selected from:
(−)2-[2-(4-chlorophenyl)benzyl]sulphinylacetamide;
(+)2-[2-(4-chlorophenyl)benzyl]sulphinylacetamide;
(−)2-[([1,1'-biphenyl]-2-ylmethyl)sulphinyl]acetamide; and
(+)2-[([1,1'-biphenyl]-2-ylmethyl)sulphinyl]acetamide;
wherein said compound has an enantiomeric excess of more than about 80%.

2. A compound according to claim 1, wherein said compound is (−)2-[2-(4-chlorophenyl)benzyl]sulphinylacetamide.

3. A compound according to claim 1, wherein said compound is (+)2-[2-(4-chlorophenyl)benzyl]sulphinylacetamide.

4. A compound according to claim 1, wherein said compound is (−)2-[([1,1'-biphenyl]-2-ylmethyl)sulphinyl]acetamide.

5. A compound according to claim 1, wherein said compound is (+)2-[([1,1'-biphenyl]-2-ylmethyl)sulphinyl]acetamide.

6. A compound according to claim 2, wherein said compound has an enantiomeric excess of more than 90%.

7. A compound according to claim 2, wherein said compound has an enantiomeric excess of more than 95%.

8. A compound according to claim 2, wherein said compound has an enantiomeric excess of 99% or more.

9. A compound according to claim 3, wherein said compound has an enantiomeric excess of more than 90%.

10. A compound according to claim 3, wherein said compound has an enantiomeric excess of more than 95%.

11. A compound according to claim 3, wherein said compound has an enantiomeric excess of 99% or more.

12. A compound according to claim 4, wherein said compound has an enantiomeric excess of more than 90%.

13. A compound according to claim 4, wherein said compound has an enantiomeric excess of more than 95%.

14. A compound according to claim 4, wherein said compound has an enantiomeric excess of 99% or more.

15. A compound according to claim 5, wherein said compound has an enantiomeric excess of more than 90%.

16. A compound according to claim 5, wherein said compound has an enantiomeric excess of more than 95%.

17. A compound according to claim 5, wherein said compound has an enantiomeric excess of 99% or more.

* * * * *